United States Patent
Chu et al.

(10) Patent No.: US 6,763,308 B2
(45) Date of Patent: Jul. 13, 2004

(54) STATISTICAL OUTLIER DETECTION FOR GENE EXPRESSION MICROARRAY DATA

(75) Inventors: Tzu-Ming Chu, Cary, NC (US); Russell D. Wolfinger, Cary, NC (US)

(73) Assignee: SAS Institute Inc., Cary, NC (US)

( * ) Notice: Subject to any disclaimer, the term of this patent is extended or adjusted under 35 U.S.C. 154(b) by 225 days.

(21) Appl. No.: 10/156,367

(22) Filed: May 28, 2002

(65) Prior Publication Data

US 2003/0225525 A1 Dec. 4, 2003

(51) Int. Cl.[7] .................. G01N 33/48; G01N 33/50
(52) U.S. Cl. .................................................. 702/19
(58) Field of Search ................ 702/19, 20; 435/4, 435/6

(56) References Cited

U.S. PATENT DOCUMENTS

| | | | |
|---|---|---|---|
| 5,143,854 A | 9/1992 | Pirrung et al. | |
| 5,571,639 A | 11/1996 | Hubbell et al. | |
| 6,132,969 A | 10/2000 | Stoughton et al. | |
| 6,229,911 B1 | 5/2001 | Balaban et al. | |
| 6,341,257 B1 * | 1/2002 | Haaland | 702/27 |
| 2002/0039740 A1 * | 4/2002 | Ramm et al. | 435/6 |
| 2003/0023148 A1 * | 1/2003 | Lorenz et al. | 600/300 |
| 2003/0023403 A1 * | 1/2003 | Nadon et al. | 702/179 |
| 2003/0144746 A1 * | 7/2003 | Hsiung et al. | 700/28 |
| 2003/0171876 A1 * | 9/2003 | Markowtiz et al. | 702/20 |
| 2003/0216870 A1 * | 11/2003 | Wolber et al. | 702/27 |

OTHER PUBLICATIONS

Schadt, Eric E., et al., "Analyzing High–Density Oligo-nucleotides Gene Expression Array Data," J.Cel. Biochem, 80 (2), 2000, pp. 192–202.

Li, Cheng et al., "Model–based analysis of oligonucleotide arrays: Expression index computation and outlier detection", Proc. Natl. Acad. Sci. USA 98 (1), 2001, pp. 31–36.

Wolfinger, Russell D., et al., "Assessing Gene Significance from cDNA Microarray Expression Data via Mixed Models," J. Compu. Biol., vol. 8, No. 6, 2001, pp. 625–637.

Chu, Tzu–Ming, et al., "A systematic statistical linear modeling approach to oligonucleotide array experiments," Mathematical Biosciences 176, 2002, pp. 35–51.

Kerr, M. Kathleen, et al., "Analysis of Variance of Gene Expression Microarray Data," Journal of Computational Biology, vol. 7, No. 6, 2000, pp. 819–837.

* cited by examiner

Primary Examiner—John Barlow
Assistant Examiner—Demetrius Pretlow
(74) Attorney, Agent, or Firm—Jones Day (57) ABSTRACT

In accordance with the disclosure below, a computer-implemented method and system are provided for detecting outliers in microarray data. A mixed linear statistical model is used to generate predictions based upon the received microarray data. Residuals are generated by subtracting model-based predictions from the original microarray sample data. Statistical tests are performed for residuals by adding covariates to the mixed model and testing their significance. Data from the microarrays are designated as outliers based upon the tested significance.

27 Claims, 14 Drawing Sheets

| CHIP | MEAN |
|---|---|
| 1 | 9.9375 |
| 2 | 9.8944 |
| 3 | 9.7913 |
| 4 | 9.8932 |
| 5 | 9.9862 |
| 6 | 9.9797 |
| 7 | 10.3464 |
| 8 | 10.1499 |

Fig. 8

| Chip | Line | Trt | Rep | Probe | Y |
|---|---|---|---|---|---|
| 1 | 1 | ir | 1 | 1 | 744.8 |
| 1 | 1 | ir | 1 | 2 | 799.5 |
| 1 | 1 | ir | 1 | 3 | 777.3 |
| 1 | 1 | ir | 1 | 4 | 678.8 |
| 1 | 1 | ir | 1 | 5 | 653.5 |
| 1 | 1 | ir | 1 | 6 | 467.5 |
| 1 | 1 | ir | 1 | 7 | 751.5 |
| 1 | 1 | ir | 1 | 8 | 644.8 |
| 1 | 1 | ir | 1 | 9 | 799.5 |
| 1 | 1 | ir | 1 | 10 | 680.3 |
| 1 | 1 | ir | 1 | 11 | 790.3 |
| 1 | 1 | ir | 1 | 12 | 688.5 |
| 1 | 1 | ir | 1 | 13 | 513.3 |
| 1 | 1 | ir | 1 | 14 | 862.5 |
| 1 | 1 | ir | 1 | 15 | 1697.3 |
| 1 | 1 | ir | 1 | 16 | 860.3 |
| 1 | 1 | ir | 1 | 17 | 936 |
| 1 | 1 | ir | 1 | 18 | 472.5 |
| 1 | 1 | ir | 1 | 19 | 544.5 |
| 1 | 1 | ir | 1 | 20 | 540.8 |
| 2 | 1 | ir | 2 | 1 | 715.3 |
| 2 | 1 | ir | 2 | 2 | 741 |
| 2 | 1 | ir | 2 | 3 | 795 |
| 2 | 1 | ir | 2 | 4 | 644.8 |
| 2 | 1 | ir | 2 | 5 | 568.5 |
| 2 | 1 | ir | 2 | 6 | 499.5 |
| 2 | 1 | ir | 2 | 7 | 662.3 |
| 2 | 1 | ir | 2 | 8 | 674 |
| 2 | 1 | ir | 2 | 9 | 797 |
| 2 | 1 | ir | 2 | 10 | 629.8 |
| 2 | 1 | ir | 2 | 11 | 753.3 |
| 2 | 1 | ir | 2 | 12 | 604 |
| 2 | 1 | ir | 2 | 13 | 524.3 |
| 2 | 1 | ir | 2 | 14 | 850.8 |
| 2 | 1 | ir | 2 | 15 | 1687.5 |
| 2 | 1 | ir | 2 | 16 | 799.5 |
| 2 | 1 | ir | 2 | 17 | 851.8 |
| 2 | 1 | ir | 2 | 18 | 503.8 |
| 2 | 1 | ir | 2 | 19 | 536.5 |
| 2 | 1 | ir | 2 | 20 | 494.3 |

| Chip | Line | Trt | Rep | Probe | Y |
|---|---|---|---|---|---|
| 3 | 1 | un | 1 | 1 | 685.3 |
| 3 | 1 | un | 1 | 2 | 762.8 |
| 3 | 1 | un | 1 | 3 | 745.3 |
| 3 | 1 | un | 1 | 4 | 634.8 |
| 3 | 1 | un | 1 | 5 | 509.8 |
| 3 | 1 | un | 1 | 6 | 462 |
| 3 | 1 | un | 1 | 7 | 638.3 |
| 3 | 1 | un | 1 | 8 | 594.5 |
| 3 | 1 | un | 1 | 9 | 769.5 |
| 3 | 1 | un | 1 | 10 | 617.3 |
| 3 | 1 | un | 1 | 11 | 9446.8* |
| 3 | 1 | un | 1 | 12 | 2755* |
| 3 | 1 | un | 1 | 13 | 436.5 |
| 3 | 1 | un | 1 | 14 | 808.8 |
| 3 | 1 | un | 1 | 15 | 1548.8 |
| 3 | 1 | un | 1 | 16 | 756 |
| 3 | 1 | un | 1 | 17 | 836 |
| 3 | 1 | un | 1 | 18 | 440.5 |
| 3 | 1 | un | 1 | 19 | 449.5 |
| 3 | 1 | un | 1 | 20 | 438 |
| 4 | 1 | un | 2 | 1 | 712.3 |
| 4 | 1 | un | 2 | 2 | 766.3 |
| 4 | 1 | un | 2 | 3 | 710 |
| 4 | 1 | un | 2 | 4 | 579.3 |
| 4 | 1 | un | 2 | 5 | 538.8 |
| 4 | 1 | un | 2 | 6 | 497.5 |
| 4 | 1 | un | 2 | 7 | 737 |
| 4 | 1 | un | 2 | 8 | 649.8 |
| 4 | 1 | un | 2 | 9 | 890.5 |
| 4 | 1 | un | 2 | 10 | 735.3 |
| 4 | 1 | un | 2 | 11 | 713.8 |
| 4 | 1 | un | 2 | 12 | 610.8 |
| 4 | 1 | un | 2 | 13 | 526 |
| 4 | 1 | un | 2 | 14 | 813.8 |
| 4 | 1 | un | 2 | 15 | 1598.8 |
| 4 | 1 | un | 2 | 16 | 790 |
| 4 | 1 | un | 2 | 17 | 953.5 |
| 4 | 1 | un | 2 | 18 | 449.8 |
| 4 | 1 | un | 2 | 19 | 485.5 |
| 4 | 1 | un | 2 | 20 | 492 |

Fig. 7A            * : OUTLIERS

| Chip | Line | Trt | Rep | Probe | Y |
|---|---|---|---|---|---|
| 5 | 2 | ir | 1 | 1 | 678.8 |
| 5 | 2 | ir | 1 | 2 | 734.3 |
| 5 | 2 | ir | 1 | 3 | 883.8 |
| 5 | 2 | ir | 1 | 4 | 621.5 |
| 5 | 2 | ir | 1 | 5 | 578.8 |
| 5 | 2 | ir | 1 | 6 | 516.5 |
| 5 | 2 | ir | 1 | 7 | 605.8 |
| 5 | 2 | ir | 1 | 8 | 618.3 |
| 5 | 2 | ir | 1 | 9 | 929.3 |
| 5 | 2 | ir | 1 | 10 | 657.3 |
| 5 | 2 | ir | 1 | 11 | 747.8 |
| 5 | 2 | ir | 1 | 12 | 655 |
| 5 | 2 | ir | 1 | 13 | 510.3 |
| 5 | 2 | ir | 1 | 14 | 864.3 |
| 5 | 2 | ir | 1 | 15 | 1656.3 |
| 5 | 2 | ir | 1 | 16 | 786.3 |
| 5 | 2 | ir | 1 | 17 | 839 |
| 5 | 2 | ir | 1 | 18 | 528.5 |
| 5 | 2 | ir | 1 | 19 | 491.3 |
| 5 | 2 | ir | 1 | 20 | 511.8 |
| 6 | 2 | ir | 2 | 1 | 684.3 |
| 6 | 2 | ir | 2 | 2 | 790.8 |
| 6 | 2 | ir | 2 | 3 | 854.3 |
| 6 | 2 | ir | 2 | 4 | 648.5 |
| 6 | 2 | ir | 2 | 5 | 553.3 |
| 6 | 2 | ir | 2 | 6 | 490.8 |
| 6 | 2 | ir | 2 | 7 | 578 |
| 6 | 2 | ir | 2 | 8 | 699.3 |
| 6 | 2 | ir | 2 | 9 | 799.5 |
| 6 | 2 | ir | 2 | 10 | 662 |
| 6 | 2 | ir | 2 | 11 | 860.8 |
| 6 | 2 | ir | 2 | 12 | 676.8 |
| 6 | 2 | ir | 2 | 13 | 473.8 |
| 6 | 2 | ir | 2 | 14 | 833 |
| 6 | 2 | ir | 2 | 15 | 1805.8 |
| 6 | 2 | ir | 2 | 16 | 836 |
| 6 | 2 | ir | 2 | 17 | 976 |
| 6 | 2 | ir | 2 | 18 | 497.5 |
| 6 | 2 | ir | 2 | 19 | 504.3 |
| 6 | 2 | ir | 2 | 20 | 495 |

| Chip | Line | Trt | Rep | Probe | Y |
|---|---|---|---|---|---|
| 7 | 2 | un | 1 | 1 | 1034 |
| 7 | 2 | un | 1 | 2 | 935 |
| 7 | 2 | un | 1 | 3 | 1176.5 |
| 7 | 2 | un | 1 | 4 | 808.3 |
| 7 | 2 | un | 1 | 5 | 743.3 |
| 7 | 2 | un | 1 | 6 | 574.5 |
| 7 | 2 | un | 1 | 7 | 911 |
| 7 | 2 | un | 1 | 8 | 786.8 |
| 7 | 2 | un | 1 | 9 | 1225.3 |
| 7 | 2 | un | 1 | 10 | 885.3 |
| 7 | 2 | un | 1 | 11 | 980.5 |
| 7 | 2 | un | 1 | 12 | 837.8 |
| 7 | 2 | un | 1 | 13 | 691.5 |
| 7 | 2 | un | 1 | 14 | 1223.3 |
| 7 | 2 | un | 1 | 15 | 2687.3 |
| 7 | 2 | un | 1 | 16 | 1243 |
| 7 | 2 | un | 1 | 17 | 1245.5 |
| 7 | 2 | un | 1 | 18 | 580.8 |
| 7 | 2 | un | 1 | 19 | 624.3 |
| 7 | 2 | un | 1 | 20 | 611.3 |
| 8 | 2 | un | 2 | 1 | 777.5 |
| 8 | 2 | un | 2 | 2 | 893 |
| 8 | 2 | un | 2 | 3 | 929.5 |
| 8 | 2 | un | 2 | 4 | 721.5 |
| 8 | 2 | un | 2 | 5 | 639.8 |
| 8 | 2 | un | 2 | 6 | 494 |
| 8 | 2 | un | 2 | 7 | 746.3 |
| 8 | 2 | un | 2 | 8 | 772.3 |
| 8 | 2 | un | 2 | 9 | 1000.8 |
| 8 | 2 | un | 2 | 10 | 726.5 |
| 8 | 2 | un | 2 | 11 | 965 |
| 8 | 2 | un | 2 | 12 | 732.3 |
| 8 | 2 | un | 2 | 13 | 602.8 |
| 8 | 2 | un | 2 | 14 | 980 |
| 8 | 2 | un | 2 | 15 | 2245 |
| 8 | 2 | un | 2 | 16 | 1014.8 |
| 8 | 2 | un | 2 | 17 | 1237.3 |
| 8 | 2 | un | 2 | 18 | 547.8 |
| 8 | 2 | un | 2 | 19 | 562 |
| 8 | 2 | un | 2 | 20 | 546 |

STATISTICAL OUTLIER DETECTION FOR GENE EXPRESSION MICROARRAY DATA

BACKGROUND OF THE INVENTION

1. Technical Field

The present invention is generally directed to the field of processing genomic data. More specifically, the invention relates to a system and method for performing statistical outlier detection for gene expression microarray data.

2. Description of the Related Art

In genomics research, gene expression arrays are a breakthrough technology enabling the measurement of tens of thousands genes' transcription simultaneously. Because the numerical data associated with expression arrays usually arises from image processing, data quality is an important issue.

Two recent scientific articles, Schadt et al. (2000) and Li and Wong (2001), discuss this data quality issue for one of the most popular expression array platforms, the Affymetrix GeneChip™. For example, they point out that outlier problems may arise due to particle contaminations (see, FIG. 1 in Schadt et al. (2000)) or scratch contaminations (see FIG. 5 in Li and Wong (2001)). They indicate that improper statistical handling of aberrant or outlying data points can mislead analysis results.

Li and Wong propose an outlier detection method based on a multiplicative statistical model. While this approach is useful, it is limited to Affymetrix data and lacks the flexibility to accommodate more complex experimental designs. The multiplicative model used by the Li and Wong is as follows:

$$Y_{ij} = \theta_i \Phi_j + \epsilon_{ij}, \quad \Sigma_j \Phi_j^2 = J, \quad \epsilon_{ij} \sim N(0, \sigma^2). \quad (1)$$

$Y_{ij}$ is the intensity measurement of the $j^{th}$ probe in the $i^{th}$ array. $\theta_i$ is the $i_{th}$ fixed array effect, $\Phi_j$ is the $j^{th}$ fixed probe effect, and J is the number of probes. The $\epsilon_{ij}$'s are assumed to be independent identically distributed normal random variables with mean 0 and variance $\sigma^2$. With the assumption of knowing $\Phi$s or $\theta$s, the following conditional means and standard errors can be derived and used in the Li and Wong method.

$$\hat{\theta}_i = \frac{\sum_j Y_{ij} \Phi_j}{\sum_j \Phi_j^2}, \quad \hat{\Phi}_j = \frac{\sum_i Y_{ij} \theta_i}{\sum_i \theta_i^2},$$

$$StdErr(\hat{\theta}_i) = \sqrt{\frac{\sum_j (Y_{ij} - \hat{Y}_{ij})^2}{J(J-1)}},$$

$$StdErr(\hat{\Phi}_i) = \sqrt{\frac{\sum_i (Y_{ij} - \hat{Y}_{ij})^2}{K(K-1)}},$$

$$K = \sum_i \hat{\theta}_i^2.$$

The following is a description of the Li and Wong outlier detection approach:

1. Check array outliers—Fit the model (1) and calculate the conditional standard errors for all $\theta_i$'s. Designate array as array outlier if either of the following criteria are met:
   i. Associated $\theta$ has standard error larger than three times the median standard error of all $\theta_i$'s.
   ii. Associated $\theta$ has dominating magnitude with square value larger than 0.8 times the sum of squares of all $\theta$s.

Select out those array outliers and go to step 2.
2. Check probe outliers—Fit the model (1) and calculate the conditional standard error for all $\Phi_j$'s. Designate probe as probe outlier if either of the following criteria are met:
   i. Associated $\Phi$ has standard error larger than three times the median standard error of all $\Phi_j$'s.
   ii. Associated $\Phi$ has dominating magnitude with square value larger than 0.8 times the sum of squares of all $\theta_j$'s.

Select out those probe outliers and go to step 3.
3. Iterate steps 1 and 2 until no further array or probe outliers selected.

SUMMARY OF THE INVENTION

In accordance with the disclosure below, a computer-implemented method and system are provided for detecting outliers in microarray data. A mixed linear statistical model is used to generate predictions based upon the received microarray data. Residuals are generated by subtracting model-based predictions from the original microarray sample data. Statistical tests are performed for residuals by adding covariates to the mixed model and testing their significance. Data from the microarrays are designated as outliers based upon the tested significance.

BRIEF DESCRIPTION OF THE DRAWINGS

The present invention satisfies the general needs noted above and provides many advantages, as will become apparent from the following description when read in conjunction with the accompanying drawings, wherein.

DETAILED DESCRIPTION

Figure 1:
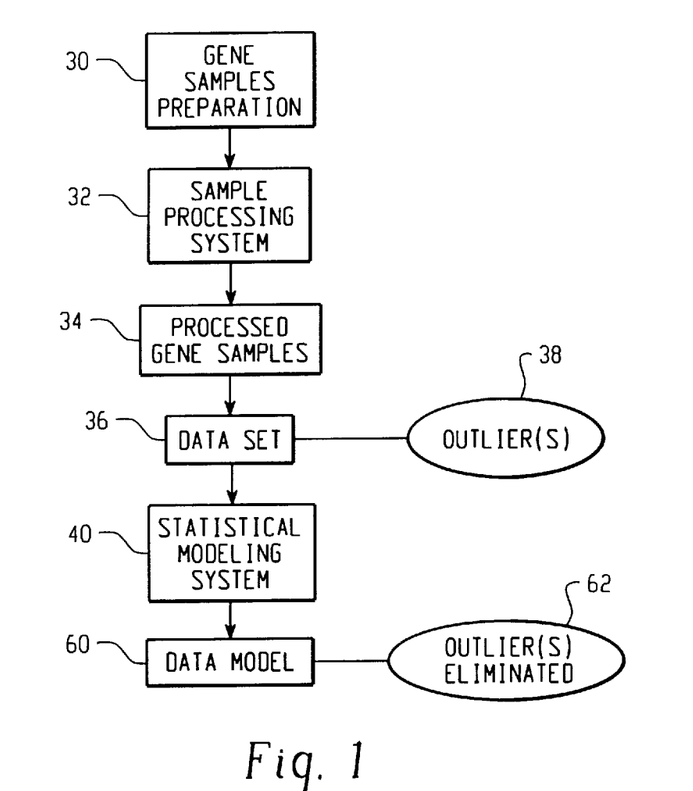
FIG. 1 is a block diagram depicting the environment of the gene sample statistical modeling system.

FIG. 1 depicts a statistical modeling system 40 for use within a gene sample analysis environment. Experimenters may wish to analyze gene samples for many reasons, such as to better understand gene hybridization under different conditions or treatments. A preliminary step in the gene analysis process is to prepare the gene samples so that they may properly undergo hybridization. Preparation 30 may include attaching gene fragments (spots) onto glass slides so as to form miniature arrays.

The prepared gene samples are processed at 32 by one of many techniques. One technique involves hybridizing the gene samples, and then processing the gene samples to obtain image intensity data, such as by reading the intensity of each spot with a fluorescent detector (or other such device such as a charge-couple device). The image data from the processed samples 34 leads to gene-specific numerical intensities representing relative expression levels, and these in turn form the data set input 36 to computational analysis designed to assess relationships across biological samples.

Figure 2:
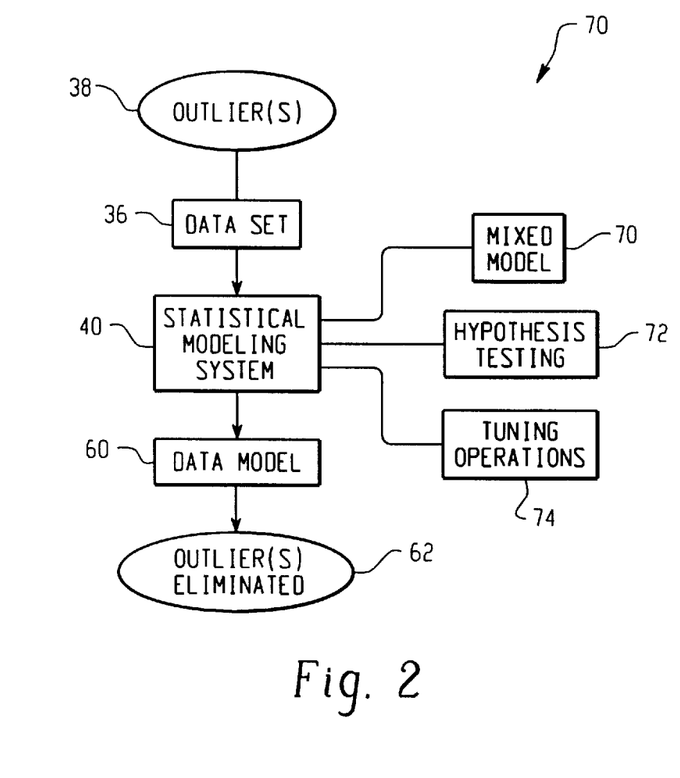
FIGS. 2 and 3 are block diagrams depicting different components of the gene sample statistical modeling system.

Due to the reasons mentioned above, the data set 36 may contain outliers 38, and therefore it is desirable to have the outliers 38 eliminated before proceeding with the computational analysis. The statistical modeling system 40 is designed to identify and eliminate outliers 38 from the data set 36 and to generate a statistical model 60 that has better predictive capability due to the outliers being eliminated 62. FIG. 2 shows additional detail of the statistical modeling system 40 performing outlier detection and elimination.

With reference to FIG. 2, the statistical modeling system 40 utilizes one or more components 70 to identify and eliminate outliers 38 from the input data set 36. One component may involve the use of a mixed linear model 62. As used herein, the term "mixed" is broadly defined as containing both fixed and random factor effects. A factor effect is fixed if all the possible levels about which inference is to be made are represented in the study. A factor is random if the levels used in the study represent only a random sample of a larger set of potential levels. The statistical modeling system 40 may also perform rigid hypothesis testing 72 on putative outliers 38. Hypothesis testing occurs after an appropriate mixed model is fit to the data set and standardized residuals are calculated and ranked according their absolute magnitude. A statistical test for the residuals can be constructed by adding additional covariates to the model, each of which is an indicator variable for the observation in question. An indicator variable contains a 1 for the particular observation and a 0 for all other observations. The method then refits the model and tests the statistical significance of the covariates to decide whether the indicated observations are indeed outliers. If they are outliers, the statistical modeling system 40 eliminates the associated observations and searches for new outliers. If they are not outliers, the outlier analysis concludes.

The hypothesis testing operation 72 can be tuned 74 to select one or more outliers at a time and to test them for statistical validity. Tuning parameters are also available for determining the size of the initial group of potential outliers and for the selectivity of the statistical test.

It should be noted that the statistical modeling system 40 may use one or more of the components to identify and eliminate outliers 38 from the data set 36. For example, the residuals may be analyzed in a way other than through hypothesis testing 72, such as by directly eliminating the data points whose residuals have absolute magnitudes larger than a predetermined threshold such as three times the estimated standard deviation.

Figure 3:
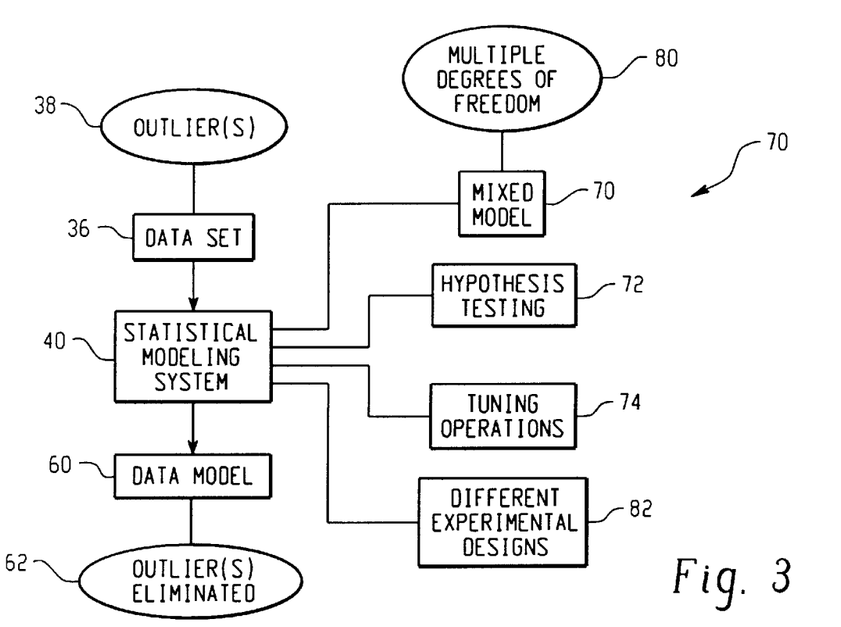

The components 70 may include additional capabilities, such as shown in FIG. 3 wherein the mixed model 70 includes effects with multiple degrees of freedom for a particular effect 80. Instead of previous approaches that are limited to a single degree of freedom (e.g., θ in model (1)), the mixed model 72 may have compound effects. For example, effects such as array, cell line, treatment, and cell line-treatment interaction may have more than two degrees of freedom. This allows greater robustness in model prediction of the data set 36 as well as an extension to accommodate different types of experimental designs (e.g., a circular design as described by Kerr and Churchill (2000), or an incomplete block and split plot design, or varying the level of replications, such as by spotting genes multiple times per array or using mRNA samples on multiple arrays, etc.).

Figure 4:
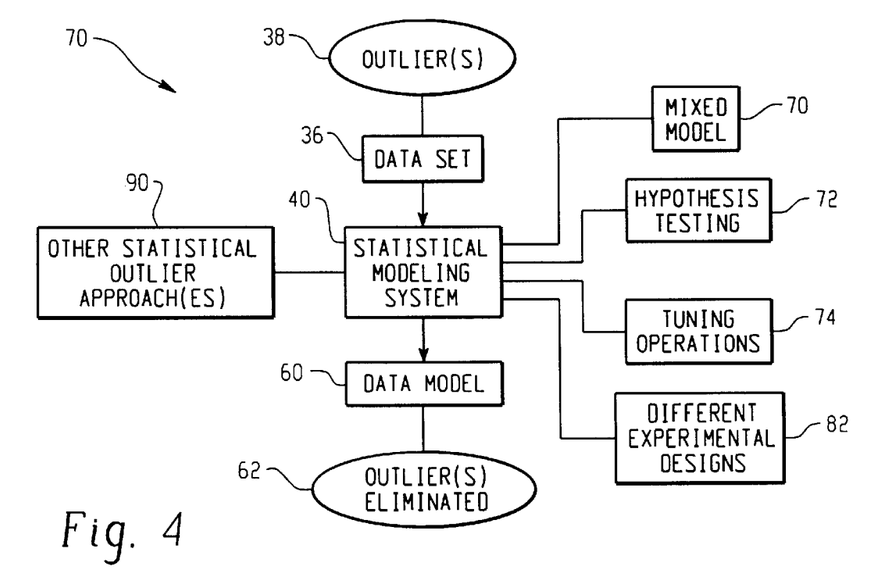
FIG. 4 is a block diagram depicting components of the gene sample statistical modeling system used with additional statistical methods.

Still further to illustrate the wide scope of the statistical modeling system 40, the statistical modeling system 40 may utilize one or more of the components 70 in combination with additional statistical approaches 90. As shown in FIG. 4, the statistical modeling system 40 may use a mixed model 70 approach (with subsequent residual analysis) in order to perform an initial outlier determination for the data set 36. The statistical modeling system 40 may then use another statistical approach 90, such as the above described Li and Wong approach (in whole or in part) to perform additional outlier analysis. It should be understood that the order of when to use other statistical approaches 90 (if at all) with respect to the components 70 may change based upon the application at hand. For example, another statistical approach 90 may first be used for outlier analysis, and then the components 70 of the statistical modeling system 40 may then provide additional outlier analysis FIGS. 5A and 5B set forth a flowchart diagram 110 showing exemplary steps and system elements of the statistical modeling system in detecting outliers associated with a GeneChip oligonucleotide microarray. The method begins with the input data 112 being fit to an appropriate mixed linear model at process block 114. From here, standardized residuals are calculated in process block 116. The standardized residuals are then compared to a predetermined cutoff (c) in decision block 118. Because the standardized residuals are typically approximately normally distributed, the cutoff here can be determined accordingly. For example, setting the cutoff at 1.96 will examine 5% of data that exhibit extreme standardized residuals. If no standardized residual is greater than the predetermined cutoff, then processing continues at process block 142 where no outliers are designated, the results from the last time fitting template model are saved for further analysis at process block 132 and the method ends at termination block 134.

Figure 5A:
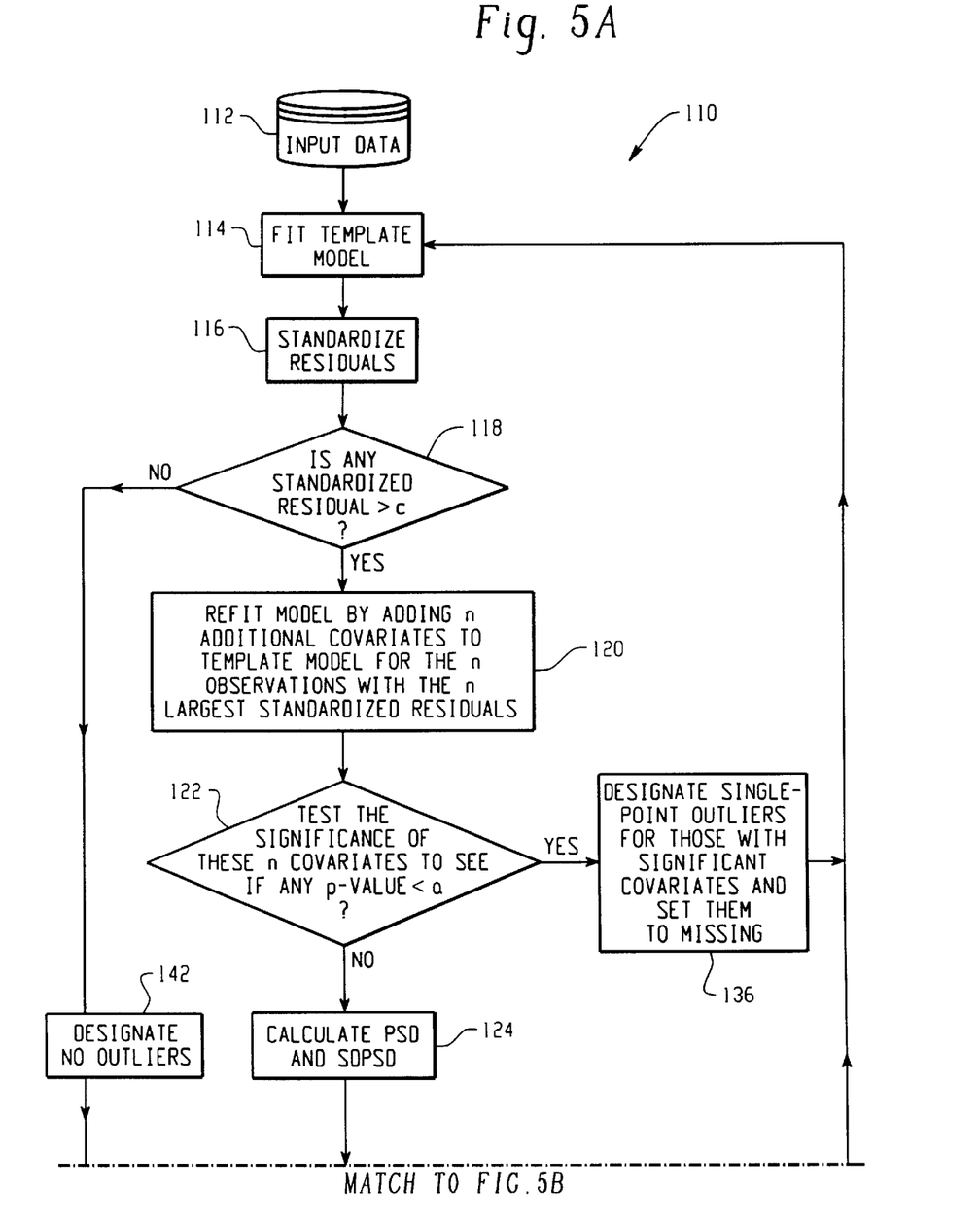
FIGS. 5A and 5B are flowcharts showing exemplary method steps and system elements for processing a GeneChip oligonucleotide microarray.
Figure 5B:
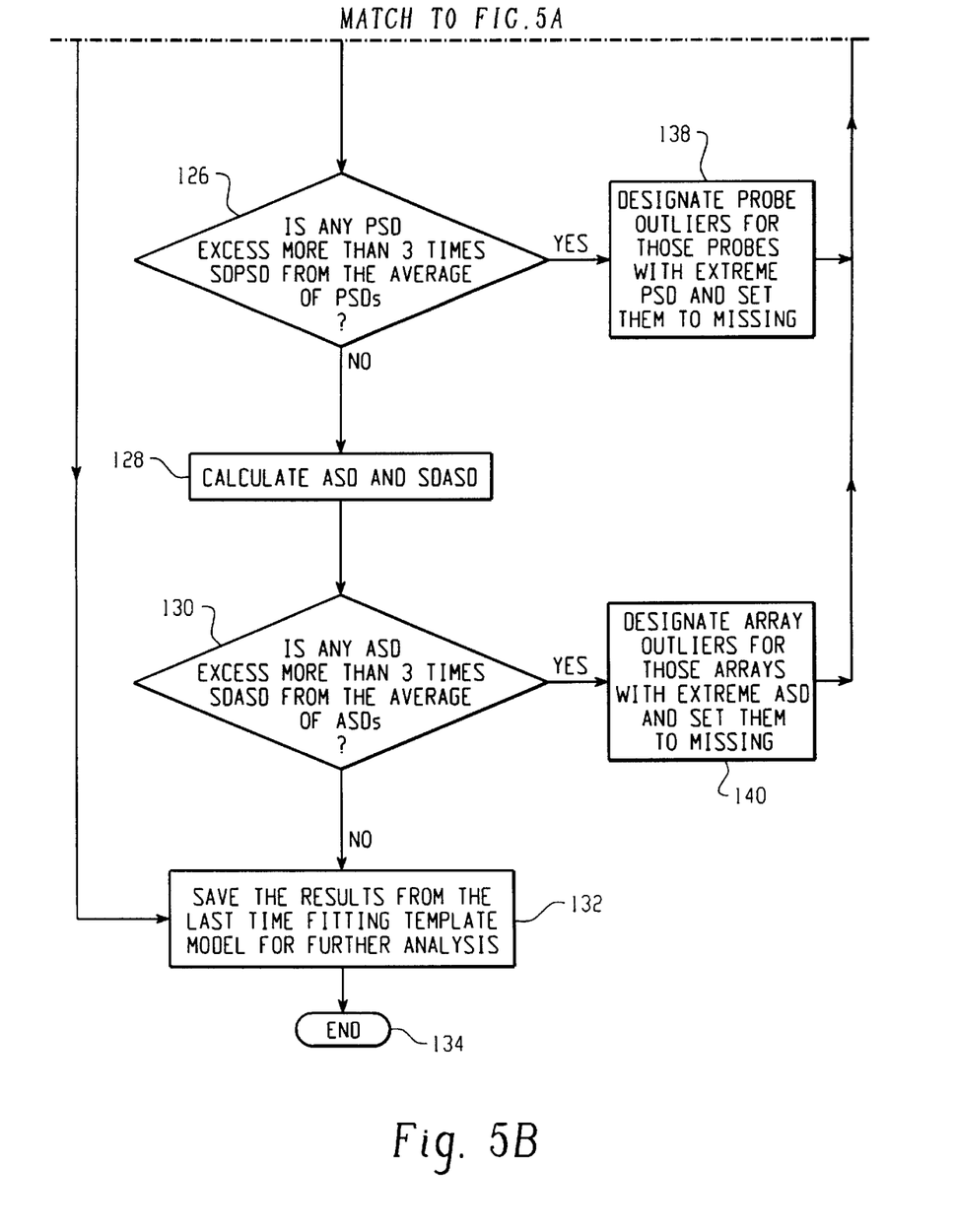

If a standardized residual is greater than the predetermined cutoff, then control passes to process block 120, where a number of outliers (n) are selected to be considered together and the model is refit with additional covariates corresponding to the indicator variables for the n observations with the largest standardized residuals in absolute value. The significances of the n covariates are tested to determine whether any calculated p-values are less than a predetermined significant level (a) at decision block 122. The model fitting and p-values can be calculated using a restricted maximum likelihood approach (see for a general discussion: Searle et al. (1993) Variance Components. Wiley, N.Y.). If the p-values are less than a, then control passes to process block 136 where observations with significant covariates are designated to be outliers and set to missing. Control passes back to process block 114, and the template model is refit with the modified data.

If the p-values are greater than a, control passes to process block 124 where the standard deviation of the standardized residual for each probe is calculated (PSD) across arrays and the standard deviation of PSD (SDPSD) are calculated across probes. Decision block 126 then tests whether any PSD exceeds three times the SDPSD from the average of the PSDs. If a PSD does exceed that amount, then process block 138 sets the probes to missing and control is returned to process block 114. If no PSDs exceed three times the SDPSD from the average of the PSDs, then control passes to process block 128.

In process block 128, a standard deviation of standardized residuals for each array (ASD) is calculated. Then, the standard deviation of ASD (SDASD) across arrays is calculated. Decision block 130 tests whether any ASD exceeds three times the SDASD from the average of the ASD. If any ASD exceeds three times the SDASD from the average of the ASD, then process block 140 sets the array to missing and returns control to process block 114. If no ASD exceeds three times the SDASD from the average of the ASD, then control passes to process block 132 where the results from the previous fitted template model are saved for further analysis and the method ends at termination block 134.

Figure 6:
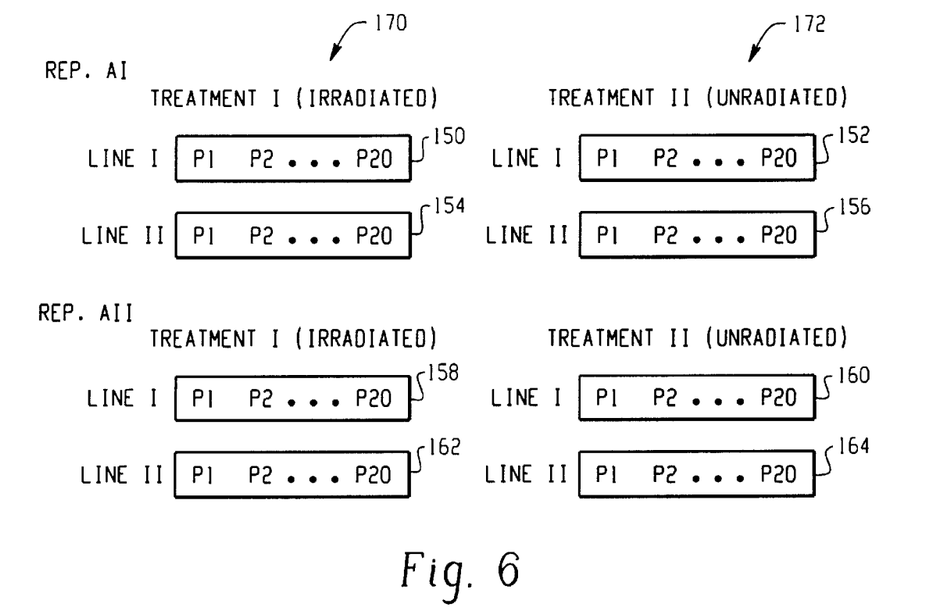
FIG. 6 is a block diagram depicting an example of a GeneChip probe design setting and experimental design layout.

FIG. 6 illustrates an exemplary GeneChip probe design setting and experimental design layout. In this example, there are eight GeneChips (150, 152, 154, 156, 158, 160, 162, and 164). Two treatments 170 and 172 were applied on two cell lines with two replicates. P1–P20 are the twenty probe intensity measurements per chip. The experiment studied the gene expression of each probe under an irradiated treatment condition and an unradiated condition. It should be understood that many different array configurations and experimental design layouts may be used and the instant configuration of FIG. 6 is only an example.

Figure 7A:
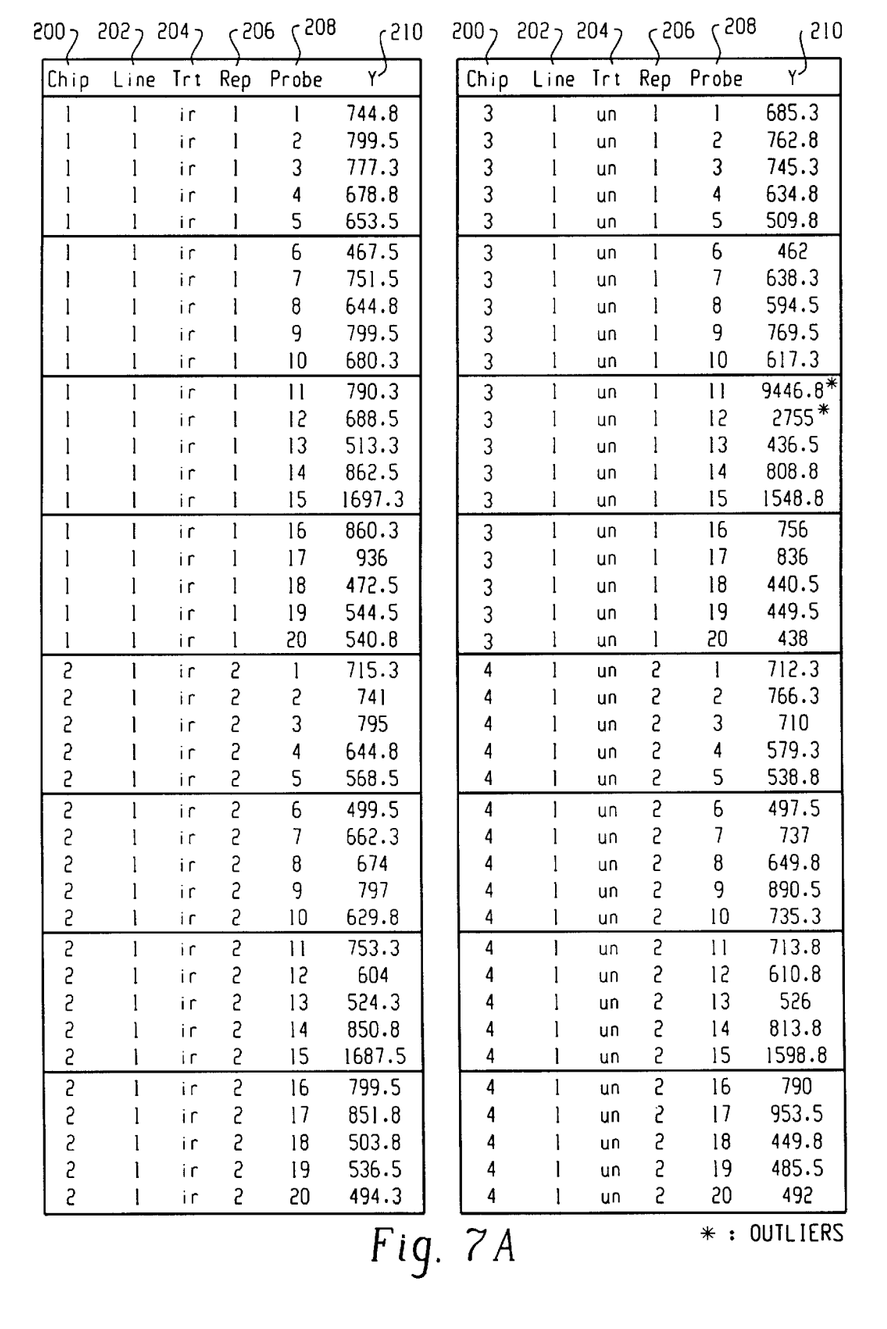
FIGS. 7A and 7B are charts depicting data resulting from processing the GeneChip probe of FIG. 6.
Figure 7B:
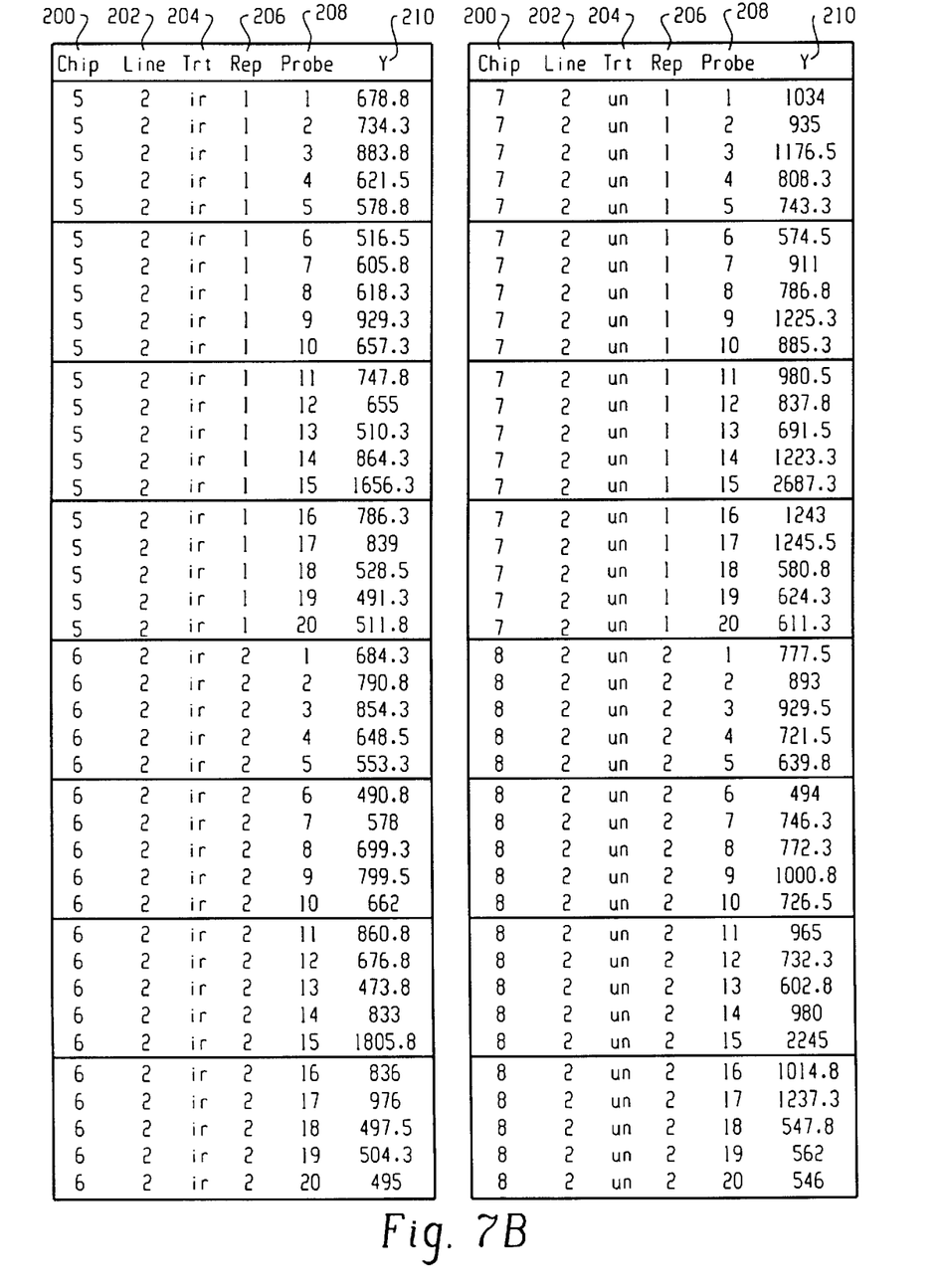

The data for this example constitute artificial expression values for one gene based on the experimental design of the ionizing radiation response data used in Tusher et al. (2001). The data set is listed in FIGS. 7A and 7B. With reference to FIGS. 7A and 7B, chip identification information is provided in column 200; line identification information is provided in column 202; treatment identification information is provided in column 204; replicate identification information is provided in column 206; probe identification information is provided in column 208; and column 210 indicates the intensity values obtained from processing the chips. As an illustration, probe #1 in line #1 of chip #1 underwent an irradiation treatment and provided an intensity value of 744.8. Of note are the two entries for probes #11 and #12 of chip #3. These are true outliers in the data set which are to be correctly identified and eliminated by the statistical modeling system while not eliminating non-outlier points from the data set.

The mixed model used in this example is as follows:

$$\log_2(Y_{ijkl}) - M_{ijl} = L_i + T_j + LT_{ij} + P_k + LP_{ik} + TP_{jk} + A_{l(ij)} + \varepsilon_{ijkl}, \quad (2)$$

$$A_{l(ij)} + \varepsilon_{ijkl} \sim N(0, \sigma_a^2 + \sigma^2),$$

$$Cov(A_{l(ij)} + \varepsilon_{ijkl}, A_{l'(i'j')} + \varepsilon_{i'j'k'l'}) =$$

$$\begin{cases} \sigma_a^2 + \sigma^2 & \text{if } (i, j, k, l) = (i', j', k', l'), \\ \sigma_a^2 & \text{if } (i, j, l) = (i', j', l') \text{ but } k \neq k', \\ 0 & \text{otherwise.} \end{cases}$$

Figure 8:
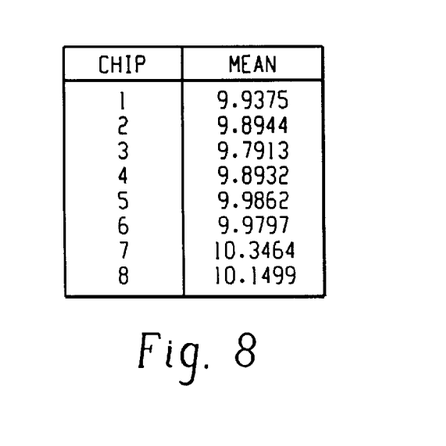
FIG. 8 is a chart depicting mean values associated with the processing of the GeneChip probe of FIG. 6.

$Y_{ijkl}$ is the expression measurement of the $i^{th}$ cell line applying the $j^{th}$ treatment at the $k^{th}$ probe in the $l^{th}$ replicate. $M_{ijl}$ is the mean value of logged (base 2) intensity of the chip associated with the $i^{th}$ cell line, the $j^{th}$ treatment, and the $l^{th}$ replicate across all genes. For this example, the eight intensity mean values are listed in FIG. 8 and used for data normalization prior to modeling. The symbols L, T, LT, P, LP, TP and A represent cell line, treatment, cell line-treatment interaction, probe, cell line-probe interaction, treatment-probe interaction, and array effects, respectively. The $A_{l(ij)}$'s are assumed to be independent and identically distributed normal random variables with mean 0 and variance $\sigma_a^2$. The $\varepsilon_{ijkl}$'s are assumed to be independent identically distributed normal random variables with mean 0 and variance $\sigma^2$, and are independent of the $A_{l(ij)}$'s. The remaining terms in the model are assumed to be fixed effects. The use of both fixed and random effects in the model allow the model to be a mixed model.

In this example, there are three tuning parameters, c, n, and a. The parameter c is used to ensure that the prospective outliers are far enough from the prediction of the model. We set c=1.645 in the example, which according to a normality assumption will result in checking the 10% most extreme standardized residuals. The parameter n is the number of outliers to consider at one time; typically n=1. The parameter a is used as the significance level for testing indicator-variable covariates. For this example, we set a=0.0026 for subsequent comparisons to the Li and Wong method because their "three standard error rule" roughly controls at the 0.0026 significance level if the standardized residuals are independent and identically distributed normal random variables. It should be understood that different parameter values may be used depending upon the application at hand.

Figures 9A, 9B, 9C:
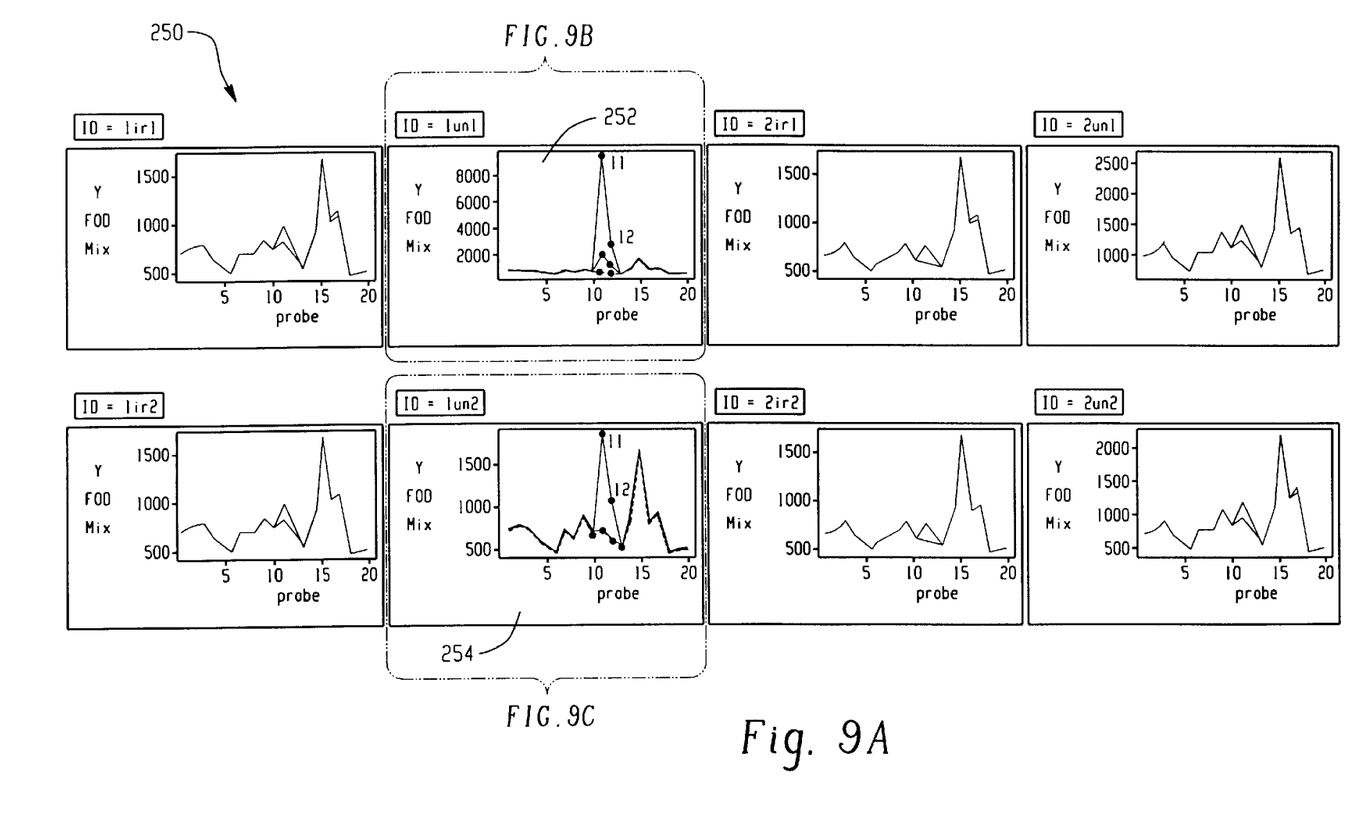
FIGS. 9A–9C show x-y graphs depicting expression profiles after using the statistical modeling system.
Figure 9B:
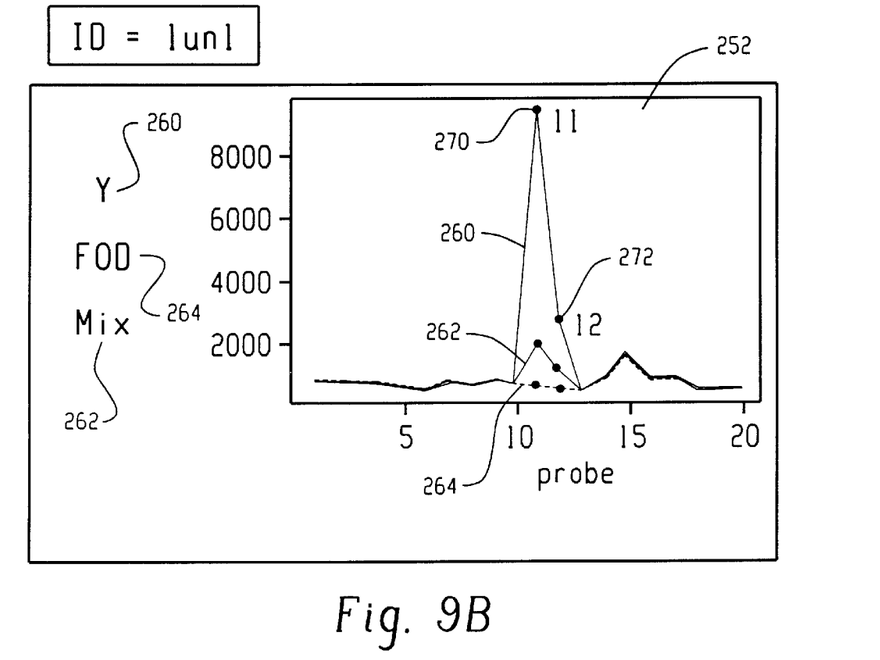
Figure 9C:
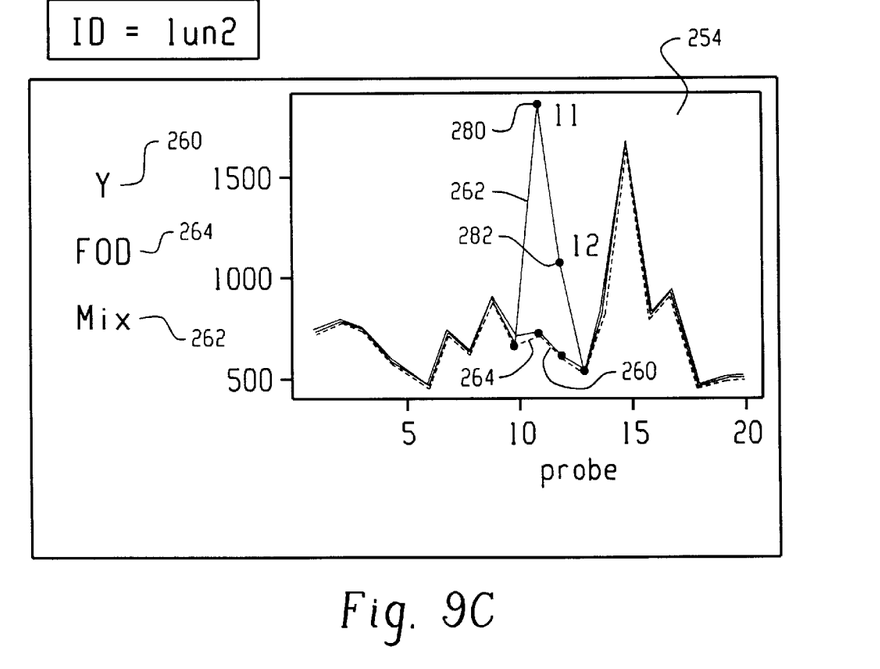

The plots 250 of FIGS. 9A–9C show the expression profiles of the gene in all eight arrays using the statistical modeling system (which is labeled in this example as "FOD" (forward outlier detection method)). The three curves in each plot 250 represent the original measurements (Y), predictions from the mixed model (Mix) after first time fitting, and predictions after the method has eliminated outliers (FOD). For example in plot 252, curve 260 depicts the original measurements (Y) for array "1un1" (i.e., the array labeled as replicate #1, line #1, with the unradiated treatment); curve 262 depicts the predictions from the mixed model (MIX); and curve 264 depicts the predictions after the method has eliminated outliers (FOD). After comparison of the original measurement curves 260 for these eight arrays, the measurements 270 and 272 of probes 11 and 12 in array "1un1" in plot 252 are determined by the FOD method to be outliers whereas the measurements 280 and 282 of plot 254 are determined not to be outliers.

Note that if the original measurement curves 260 and mix curves 262 for plots 252 and 254 are compared, then both probe 11 at 270 in plot 252 and probe 11 at 280 in plot 254 will be selected as outliers if selecting multiple outliers at each time. In this case, the FOD method only selects probes 11 and 12 in array 1un1 as single-point outliers.

Figure 10A:
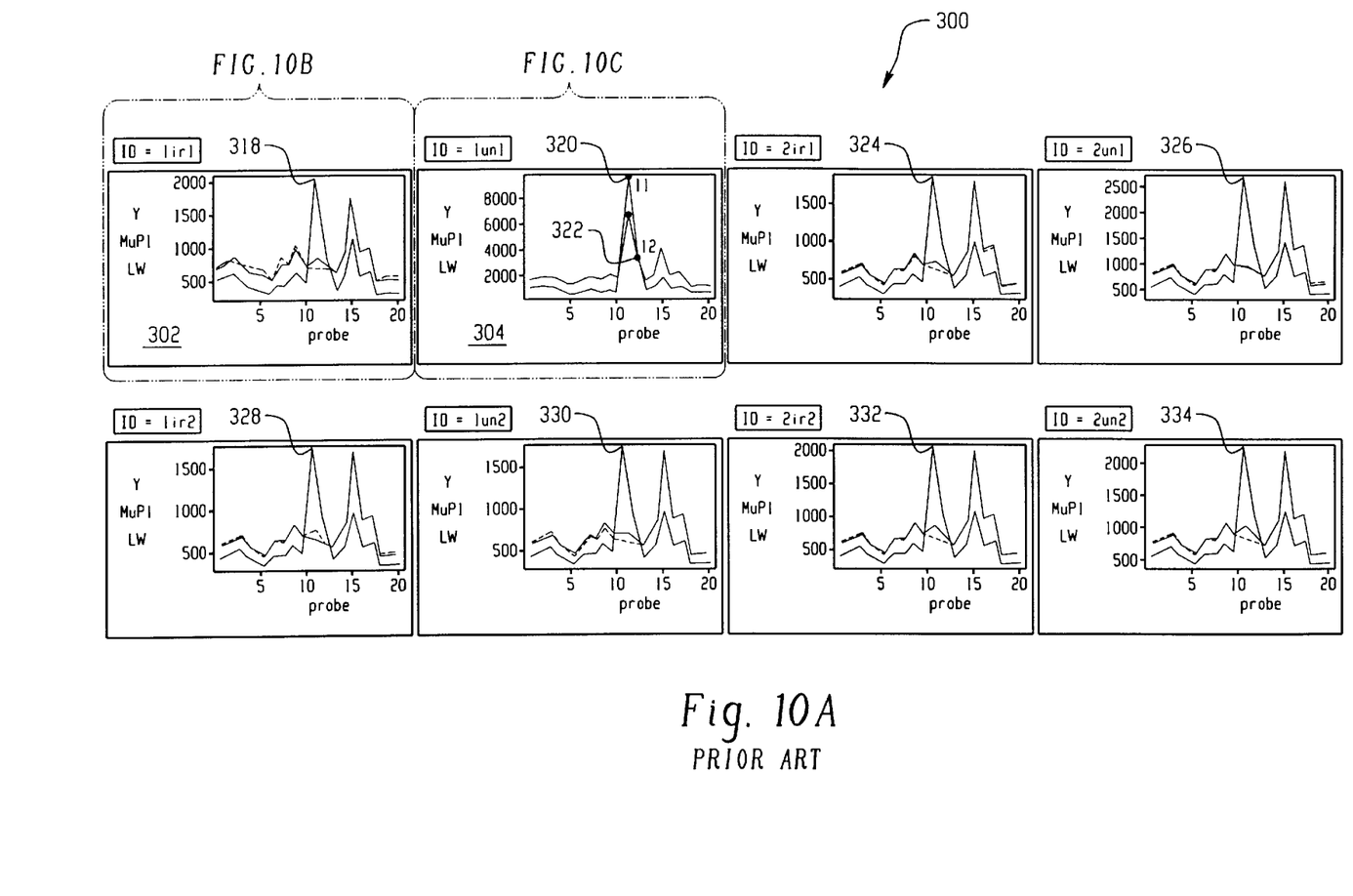
FIGS. 10A–10C show x-y graphs depicting expression profiles after using a prior art gene sample processing system.
Figure 10B:
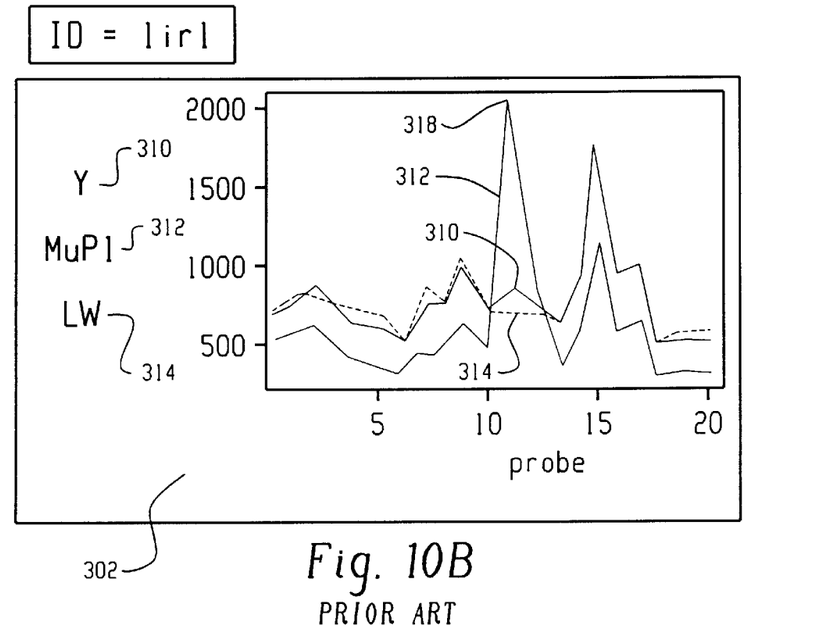
Figure 10C:
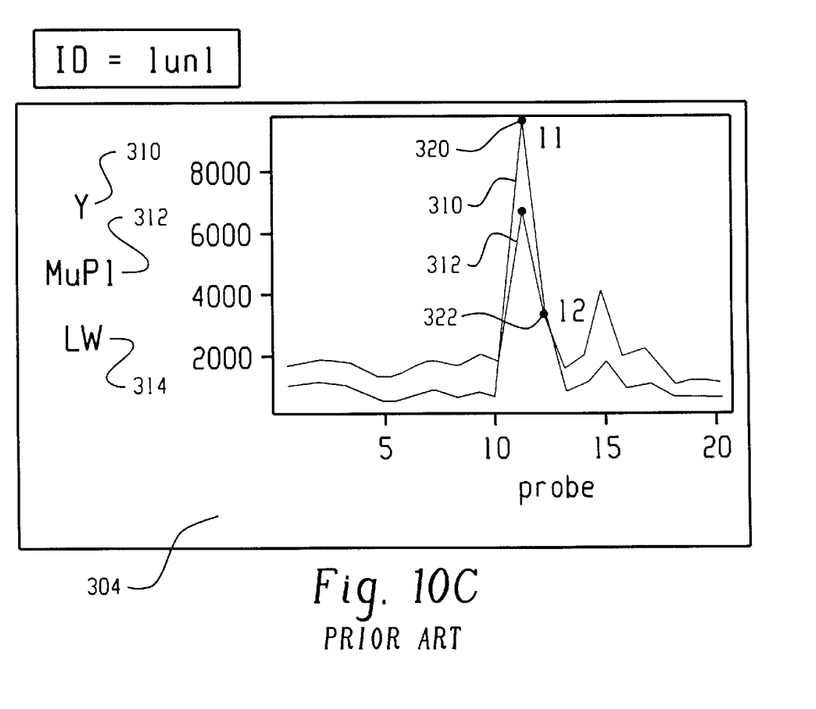

The plots 300 of FIGS. 10A–10C show the expression profiles of the gene in the eight arrays described in FIGS. 9A–9C. The expression profiles of FIGS. 10A–10C were generated using model (1) and the outlier detection approach disclosed in Li and Wong (2001). The three curves in each plot 300 represent the original measurements (Y), predictions from model (1) (MuP1) after first time fitting, and predictions after applying the LW outlier detection approach (LW). For example in plot 302, curve 310 represents the original measurements (Y); curve 312 represents predictions from model (1) (MuP1) after first time fitting; and curve 314 represents predictions (LW) after applying the LW outlier detection approach.

In this case, the LW approach selects no array outlier but "probe 11" 320 of all eight arrays (318, 320, 324, 326, 328, 330, 332, 334) as probe outliers in the first iteration. After eliminating "probe 11" 320, the "probe 12" 322 makes the within array standard error of array "1un1" 304 about six times larger than the median within array standard error. Therefore, the LW approach further selects the entire array "1un1" 304 as array outliers in the second iteration. In total, the LW approach selects twenty-seven observations as outliers. However, note that if "probe 11" 320 and "probe 12" 324 in array "1un1" 304 are removed from the data set, then the LW approach does not select any outliers. Thus, under model (1) and the LW approach, "probe 11" 320 and "probe 12" 324 in array "1un1" 304 are two extremely influential observations which cause the incorrect classification of the other twenty-five observations as outliers by this approach. This may be due to the LW approach not examining single-point outliers first, but rather applying the "3 standard error rule" and then conservatively selecting array and probe outliers (which actually result from few of the single-point outliers as described in the example). Table 1 highlights additional differences between FOD and LW.

TABLE 1

$R^2$ and Estimates comparisons.

|  |  |  | MuPI | LW | MIX | FOD |
|---|---|---|---|---|---|---|
| $R^2$ |  |  | 0.2987 | 0.8461 | 0.7624 | 0.9883 |
| % of Data Used |  |  | 100 | 83.13 | 100 | 97.5 |

|  |  |  | Estimate | p-value | Estimate | p-value |
|---|---|---|---|---|---|---|
| Line Effect | n/a | n/a | 0.1265 | 0.1795 | 0.0502 | 0.0154 |
| Trt Effect | n/a | n/a | −0.0921 | 0.3023 | −0.0158 | 0.2707 |
| Line*Trt Interaction | n/a | n/a | −0.0921 | 0.5858 | 0.0605 | 0.0708 |

MuPI: applying multiplicative model without eliminating outlier(s);
LW: applying multiplicative model with eliminating outlier(s) by the LW approach;
MIX: applying mixed model without eliminating outlier(s); and
FOD: applying mixed model with eliminating outlier(s) by the FOD approach.

Figure 11:
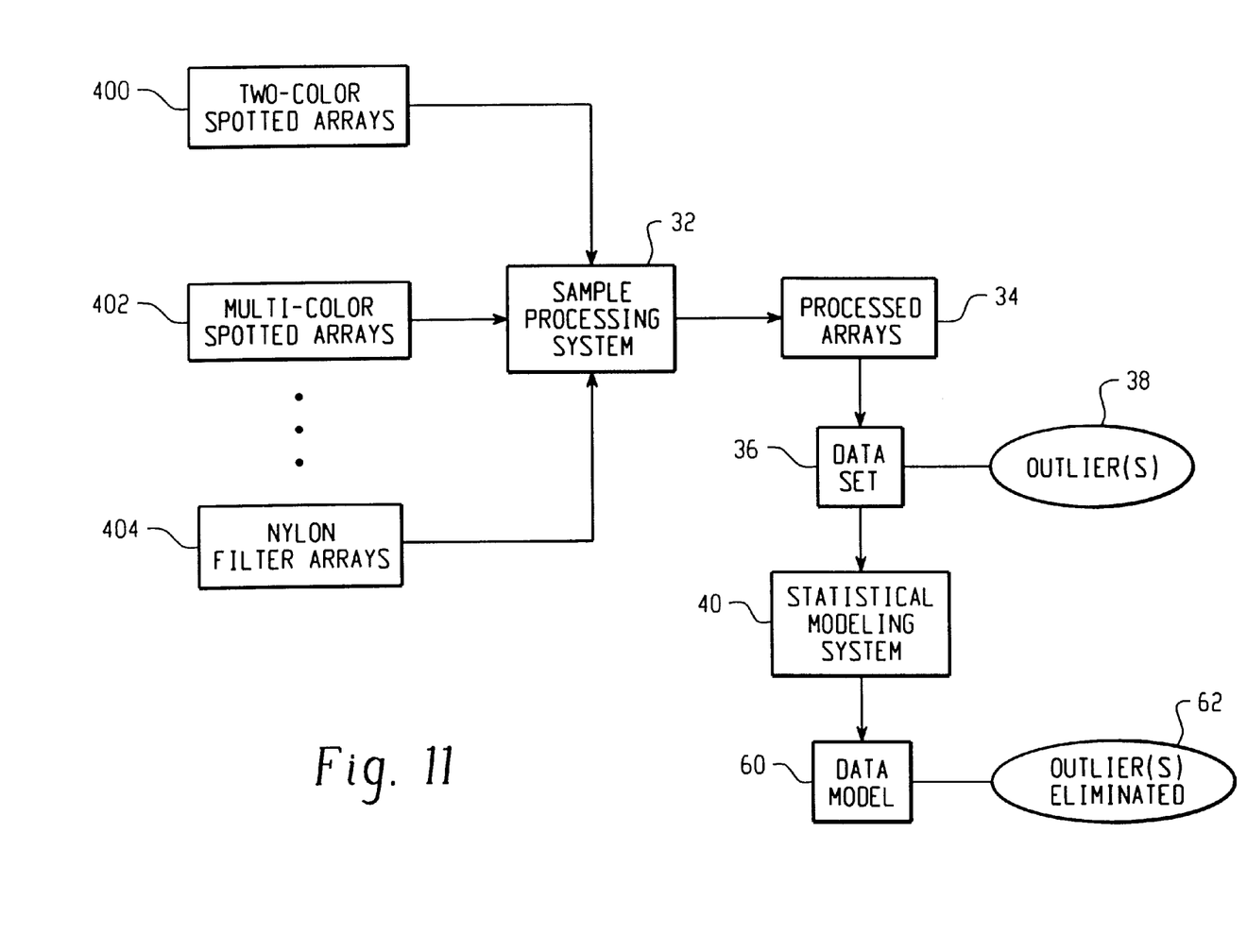
FIG. 11 is a block diagram depicting use of a number of different arrays with the statistical modeling system.

The preferred embodiment described with reference to the drawing figures is presented only to demonstrate examples of the invention. Additional and/or alternative embodiments of the invention should be apparent to one of ordinary skill in the art upon reading this disclosure as the present invention is applicable in many contexts. As an example of the wide scope of the invention, FIG. 11 depicts the statistical modeling system 40 detecting outliers in data arising from any kind of gene expression microarray platform (such as two-color spotted arrays 400, multi-color spotted arrays 402, nylon filter arrays 404, etc.).

Figure 12:
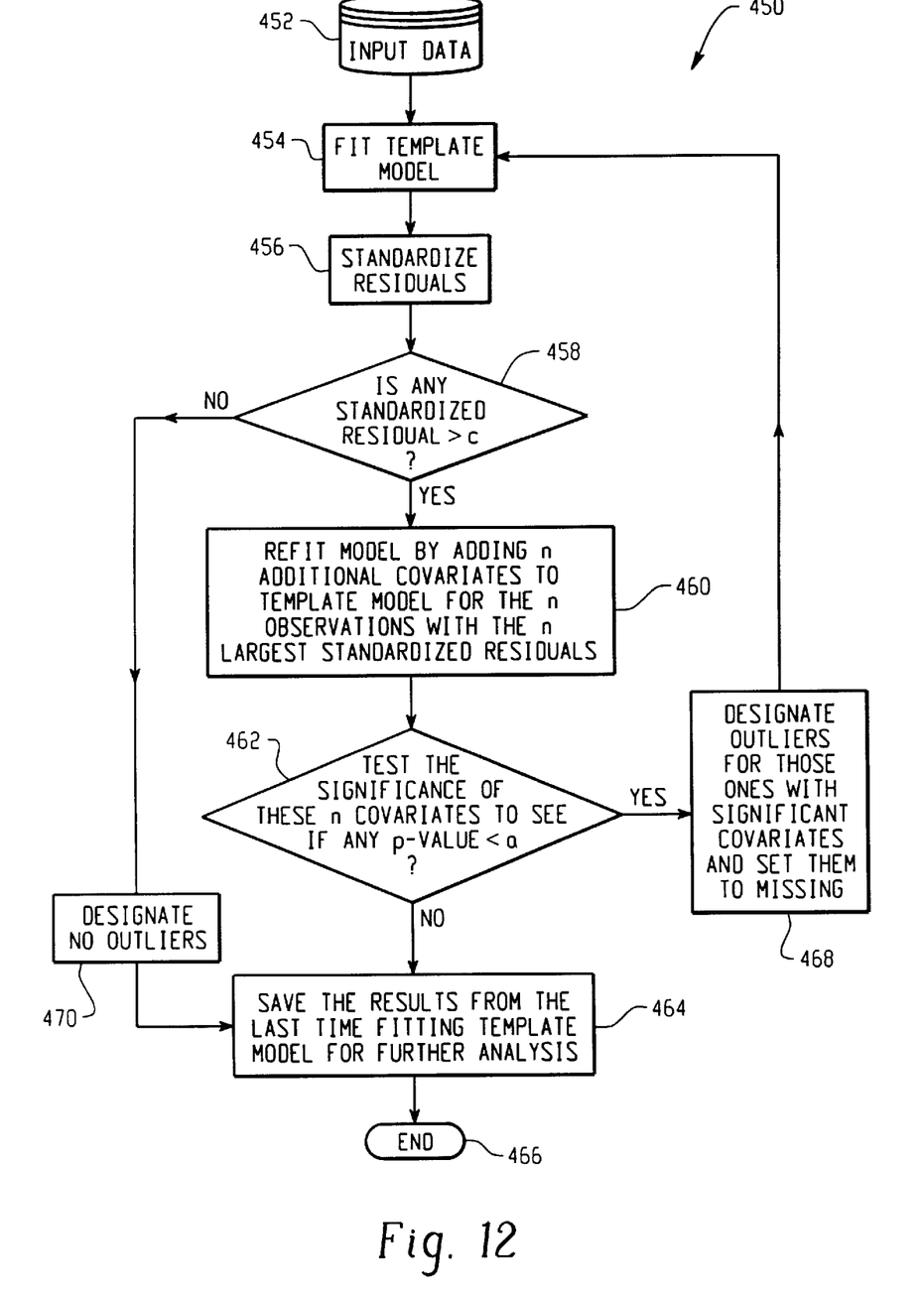
FIG. 12 is a flowchart showing exemplary method steps and system elements for processing a cDNA microarray.

For example, the statistical modeling system and method may process data from cDNA microarrays. Processing for of this type of microarray is shown by the flowchart 450 of FIG. 12. With reference to FIG. 12, the method begins with the input data 452 being fit to an appropriate mixed linear model at process block 454. From here, standardized residuals are calculated in process block 456. The standardized residuals are then compared to a predetermined cutoff (c) in decision block 458. Because the standardized residuals are distributed by standard normal, the cutoff here may be determined according to this normality. For example, setting the cutoff at 1.96 will examine 5% of data that exhibit extreme standardized residuals. If no standardized residual is greater than the predetermined cutoff, then processing continues at process block 470 where no outliers are designated, the results from the previous fitted template model are saved for further analysis at process block 464 and the method ends at termination block 466.

If a standardized residual is greater than the predetermined cutoff, then control passes to process block 460, where a number of outliers (n) are selected to be considered together and the model is refit with additional covariates corresponding to the indicator variables for the n observations with the largest standardized residuals in absolute value. The significance of the n covariates are tested to determine whether any calculated p-values are less than a predetermined p-value (a) at decision block 462. If the p-values are less than a, then control passes to process block 468 where observations with significant covariates are set to missing. Control passes back to process block 454 and a new model is fit to the remaining covariates. If the p-values are greater than a, then the results from the previous fitted template model are saved for further analysis at process block 464 and the method ends at termination block 466.

Figure 13:
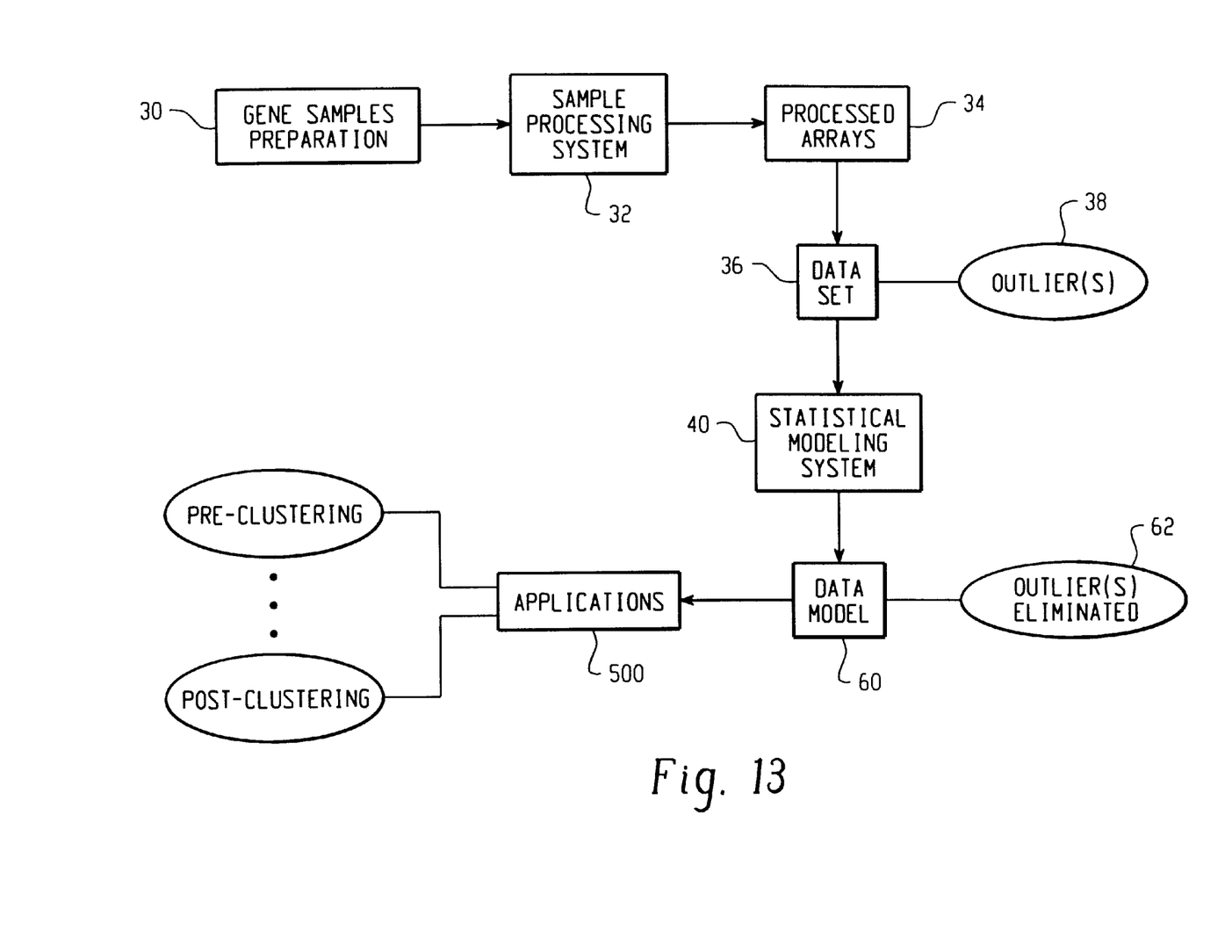
FIG. 13 is a block diagram depicting use of the statistical modeling system with a number of applications.

As yet another example of the wide scope of the system and method, FIG. 13 shows use of the statistical modeling system with a number of different applications 500. For example, the data model 60 (with outliers eliminated) may be used in any subsequent analysis, such in cluster analysis. More specifically, experimenters may use the data model 60 as a precursor to clustering to ensure the inputs are statistically meaningful, or it can be used after clustering to explore and validate implied associations. It should be understood that not only may the generated data models be used by different applications, but also the original data set (with outliers eliminated) may be used.

It is claimed:

1. A computer-implemented method for detecting outliers in microarray data, said method comprising the steps of:
   receiving the microarray data, said microarray data containing data values indicative of at least one characteristic associated with processed gene samples;
   using a mixed linear statistical model to generate predictions based upon the received microarray data;
   generating residuals based upon the predictions and the received microarray data;
   performing a statistical test for at least one generated residual by adding covariates to the mixed linear mathematical model and testing significance of the covariates; and
   designating a data value within the received microarray data as an outlier based upon the tested significance.

2. The method of claim 1 wherein the microarray data was obtained by processing gene fragments located on miniature arrays.

3. The method of claim 1 wherein the method may designate data values as outliers that arise from at least two arrays selected from the group consisting of oligonucleotide arrays, two-color spotted cDNA arrays, multi-color spotted arrays, and nylon filter radiolabeled arrays.

4. The method of claim 1 wherein the data values are image intensity data values.

5. The method of claim 4 wherein the image intensity data values are indicative of gene expression levels.

6. The method of claim 1 further comprising the step of:
   generating a mathematical data model to predict the received microarray data without the designated outlier data value being considered in the data model generation.

7. The method of claim 6 wherein the generated mathematical data model is a mixed linear statistical model.

8. The method of claim 1 wherein the mixed linear statistical model includes both fixed and random effects associated with processing gene-related samples.

9. The method of claim 1 wherein the mixed linear statistical model can include effects with multiple degrees of freedom and their interactions.

10. The method of claim 9 wherein the mixed linear statistical model is extensible to different types of experimental designs.

11. The method of claim 1 further comprising the steps of:
determining a dataset of the generated residuals based upon their absolute magnitude, wherein the residuals are associated with observations in the received microarray data; and
performing the statistical test on the residual subset by adding covariates to the mixed linear mathematical model, wherein each of the added covariates is an indicator variable for the observation in question.

12. The method of claim 11 further comprising the steps of:
refitting the mixed linear mathematical model and testing the statistical significance of the covariates to determine whether their associated observations are outliers; and
if their associated observations are determined to be outliers, then eliminating the associated observations.

13. The method of claim 12 further comprising the step of:
selecting a parameter that controls the number of observations to be tested for being an outlier.

14. The method of claim 13 further comprising the step of:
selecting a parameter that controls the selectivity of the statistical test to be used in testing the statistical significance of the covariates.

15. The method of claim 14 further comprising the step of:
selecting a parameter that controls the number of the residuals to be used within the dataset.

16. The method of claim 14 further comprising the step of:
selecting a parameter that establishes a threshold for determining whether a residual is to be added to the dataset.

17. The method of claim 12 wherein an additional outlier detection means is used to determine which of the data values are outliers.

18. The method of claim 1 further comprising the steps of:
eliminating from the received data the data values whose residuals have their absolute magnitudes satisfy a predetermined criterion; and
refitting the mixed mathematical model with the received data after the data values have been eliminated.

19. The method of claim 1 wherein the data set without the designated outlier data value is used in computational analysis designed to assess relationships across gene-related samples.

20. The method of claim 1 wherein a data model is generated without the designated outlier data value being considered, said generated data model being used in association with cluster analysis.

21. A computer-implemented method for detecting outliers in microarray data, said method comprising the steps of:
receiving the microarray data, said microarray data containing data values indicative of at least one characteristic associated with processed gene samples;
using a statistical model to generate predictions based upon the received microarray data, wherein the statistical model includes multiple degrees of freedom;
generating residuals by comparing the predictions with the received microarray data;
performing a statistical test for at least one generated residual by adding covariates to the mathematical model and testing significance of the covariates; and
designating a data value within the received microarray data as an outlier based upon the tested significance.

22. The method of claim 21 wherein the statistical model includes a variable to model a gene-sample related interaction.

23. The method of claim 22 wherein the statistical model is a mixed statistical model.

24. A computer-implemented method for detecting outliers in microarray data, said method comprising the steps of:
receiving the microarray data, said microarray data containing data values indicative of at least one characteristic associated with processed gene samples;
using a mixed mathematical model to generate predictions based upon the received microarray data;
generating residuals by comparing the predictions with the received microarray data; and
designating a data value within the received microarray data as an outlier based upon the magnitude of the generated residuals.

25. A computer-implemented apparatus for detecting outliers in microarray data, comprising:
means for receiving the microarray data, said microarray data containing data values indicative of at least one characteristic associated with processed gene samples;
means for using a mixed mathematical model to generate predictions based upon the received microarray data;
means for generating residuals by comparing the predictions with the received microarray data; and
means for designating a data value within the received microarray data as an outlier based upon the magnitude of the generated residuals.

26. A computer-implemented statistical system for analyzing microarray data, said microarray data containing data values indicative of at least one characteristic associated with processed gene samples, said system comprising:
a mixed linear statistical model that generates predictions based upon the received microarray data,
wherein residuals are generated based upon the predictions and the received microarray data;
a statistical test to be performed for at least one generated residual by adding covariates to the mixed linear mathematical model,
wherein the significance of the covariates are tested, wherein a data value within the received microarray data is designated as an outlier based upon the tested significance.

27. The system of claim 26 further comprising:
a gene samples preparation system for preparing gene samples for analysis; and
a sample processing system that processes the prepared gene samples, wherein the microarray data is generated by the sample processing system.

* * * * *